United States Patent
Peeters

(10) Patent No.: US 6,762,056 B1
(45) Date of Patent: Jul. 13, 2004

(54) RAPID METHOD FOR DETERMINING POTENTIAL BINDING SITES OF A PROTEIN

(75) Inventor: John P. Peeters, Bethesda, MD (US)

(73) Assignee: Protiveris, Inc., Rockville, MD (US)

( * ) Notice: Subject to any disclaimer, the term of this patent is extended or adjusted under 35 U.S.C. 154(b) by 462 days.

(21) Appl. No.: 09/859,027

(22) Filed: May 16, 2001

Related U.S. Application Data

(63) Continuation-in-part of application No. 09/547,777, filed on Apr. 12, 2000, now Pat. No. 6,325,904, which is a continuation of application No. 09/044,350, filed on Mar. 19, 1998, now Pat. No. 6,123,819.
(60) Provisional application No. 60/204,742, filed on May 17, 2000, and provisional application No. 60/065,373, filed on Nov. 12, 1997.

(51) Int. Cl.[7] ............................................. G01N 33/00
(52) U.S. Cl. ....................................................... 436/86
(58) Field of Search .......................................... 436/86

(56) References Cited

U.S. PATENT DOCUMENTS

| | | | |
|---|---|---|---|
| 4,513,308 A | 4/1985 | Greene et al. ................. 357/55 |
| 4,724,318 A | 2/1988 | Binnig ......................... 250/306 |
| 5,096,676 A | 3/1992 | McPherson et al. ........ 422/245 |
| 5,202,290 A | 4/1993 | Moskovits |
| 5,316,979 A | 5/1994 | MacDonald et al. ........ 437/203 |
| 5,419,278 A | 5/1995 | Carter ......................... 117/206 |
| RE35,317 E | 8/1996 | Lindsay ..................... 250/307 |
| 5,641,681 A | 6/1997 | Carter ........................... 436/4 |
| 5,643,540 A | 7/1997 | Carter et al. ............. 422/245.1 |
| 5,846,708 A | 12/1998 | Hollis et al. ................... 435/6 |
| 5,961,934 A | 10/1999 | Arnowitz et al. ........ 422/245.1 |
| 6,057,543 A | 5/2000 | Vestal et al. ................ 250/282 |

FOREIGN PATENT DOCUMENTS

| | | |
|---|---|---|
| DE | 4422049 A1 | 1/1996 |
| WO | WO 94/29708 | 12/1994 |
| WO | WO 97/34140 | 9/1997 |

OTHER PUBLICATIONS

Dufrêne et al. "Influence of Substratum Surface Properties on the Organization of Adsorbed Collagen Films: In Situ Characterization by Atomic Force Microscopy", Langmuir, 1999, v. 156, pp. 2871–2878.*

Galli et al. "Protein adsoprtion on topographically nano-structred titanium", Surface Acience, 2001, 474, L180–L184.*

Galli et al. "Creation of nanostructures to study the topographical dependency of protein adsorption",Colloids and Surfaces B: Bionterfaces, 2002, 26, pp. 255–267.*

(List continued on next page.)

*Primary Examiner*—Yelena G. Gakh
(74) *Attorney, Agent, or Firm*—Sonia K. Guterman; Mintz, Levin, Cohn, Ferris, Glovsky and Popeo, P.C.

(57) ABSTRACT

A method for discovering proteins and protein geometries, and a method for conducting whole proteome assays on a single test surface are disclosed. A test surface is provided featuring a surface containing a random distribution of randomly shaped features of a size from $10^{-10}$ meters to $10^{-8}$ meters in width, height, depth, and spacing. A sample containing proteins is provided to interact with the test surface long enough for protein molecules to locate and adsorb to complementary sites on the test surface. Unadsorbed proteins are washed away. Protein adsorption sites are then discovered using a means such as an atomic force microscope (AFM) to identify locations where proteins are adsorbed to the surface. The topology of the protein adsorption sites is precisely measured using an AFM. Protein surface topology is deduced by determining the complementary surface to the protein adsorption sites. A device that is diagnostic for a disease is prepared by determining the disease-specific adsorption site pattern on a given test surface, in contrast to the non-disease pattern.

20 Claims, 6 Drawing Sheets

OTHER PUBLICATIONS

Denis et al. "Protein Adsorption on Model Surfaces with Controlled Nanotopography and Chemistry", Langmuir 2002, 18, pp. 819–828.*

First, P.N. et al., "Metallicity and Gap States in Tunneling to Fe Clusters on GaAs(110)," Physical Review Letters, vol. 63, No. 13, pp. 1416–1419, Sep. 25, 1989.

Sidles, J.A. et al., "Magnetic Resonance Force Microscopy," Rev.Mod. Phys. vol. 67, No. 1, pp. 249–265, Jan. 1995.

Kolb et al., Nanofabrication of Small Copper Clusters on Gold (111) Electrodes by a Scanning Tunneling Microscope, Science, vol. 275, pp. 1097–1099, Feb. 21, 1997.

"IBM's tiny microdrive promises to put big storage space into devices like digital cameras and PDAs," Popular Science, p. 38, Dec. 1998.

Weiss, Shimon, "Fluorescence Spectroscopy of Single Biomolecules," Science Magazine, vol. 283, pp. 1676–1683, Mar. 12, 1999.

Robbie et al., "Thin Films with Nanometer–Scale Pillar Microstructure," Journal or Material Research, vol. 14, No. 7, pp. 3158–3163, Jul. 1999.

Vettiger et al., "The 'Millipede'–More than one thousand tips for future AFM data storage," IBM Journal of Research & Development, vol. 44, No. 3, Nov. 22, 1999.

de Lozanne, Alex, "You May Squeeze the Atoms But Don't Mangle the Surface", Science, vol. 291, No. 5513, pp. 2561–2562, Mar. 30, 2001.

* cited by examiner

RAPID METHOD FOR DETERMINING POTENTIAL BINDING SITES OF A PROTEIN

CROSS-REFERENCE TO RELATED APPLICATIONS

The present application claims the benefit of U.S. provisional application serial No., 60/204,742, filed May 17, 2000, and is a continuation-in-part of U.S. patent application Ser. No. 09/547,777 filed Apr. 12, 2000, now U.S. Pat. No. 6,325,904, issued Dec. 4, 2001, which is a continuation application of Ser. No. 09/044,350, filed Mar. 19, 1998, now U.S. Pat. No. 6,123,819, issued Sep. 26, 2000, which claims priority to U.S. provisional application No. 60/065,373, filed Nov. 12, 1997, all of which are hereby incorporated in their entirety by reference herein.

BACKGROUND OF THE INVENTION

The present invention relates generally to the field of sensors for the detection and investigation of proteins, pathogens and other biologically important molecules, and more particularly to a bionanotechnology method for rapidly determining the surface topology of protein molecules.

Determining the surface topology of proteins is vitally important to broad fields of science including pharmaceutical research and genomics, as well as fundamental research into biological processes. Surface topology determines how proteins interact with each other, since proteins of complementary shape tend to bind together while proteins of non-complementary shapes do not. This lock-and-key binding of proteins provides the mechanisms by which enzymes, antibodies and nucleic molecules accomplish their vital biological functions, as well as the mechanisms that enable viruses and bacteria to infect cells. Knowing the shape and surface characteristics of a protein can help explain its function in a cell. Also, knowing the surface topology of a protein permits the development of drugs and sensors that will bind with that particular protein, enabling more effective medications and diagnostic tests for the treatment of human diseases.

Understanding the surface topology of biologically significant proteins is an important step towards the development of new medicines and medical treatments. Once the shape and chemical structure of a protein is known, pharmaceutical researchers can design a complementary molecule that will fit into the surface folds of the protein and bind to it just as an antibody binds to an antigen. Then pharmaceutically active molecules can be attached to the binding molecule to deliver a specific medication to a particular cell, bacterium or virus.

Understanding the surface topology of proteins is also essential to the development of sensitive diagnostic and protein assay methods. With the rapid advances of biotechnology and genetic research, which are elucidating the key roles and the presence of particular proteins that can be characteristic of certain disease states, great emphasis has been placed on developing very sensitive assays and sensor methods capable of detecting minute quantities of biologically significant molecules. The detection and quantification of specific proteins associated with a given disease, such as a given cancer, may enable much earlier detection and treatment. Furthermore, the ability to detect nucleic acid sequences encoding particular proteins enables many beneficial medical and commercial applications, including agricultural product screening and development. However, in many applications, methods used to detect particular proteins still require an understanding of the binding sites and surface topology of the protein.

The primary method used to develop an understanding of protein surface topologies is protein X-ray crystallography. X-ray crystallography makes use of the diffraction of X-rays by protein crystals to determine the precise three-dimensional arrangement of atoms within the protein molecule. Sophisticated analysis software and algorithms permit researchers to translate the diffraction patterns into three-dimensional structural information, and from that to identify the surface topology of the protein.

Before a protein can be studied with X-ray crystallography, the protein must be isolated, purified and crystallized. Because of the molecular complexity of proteins, obtaining suitable crystals for crystallography can be quite difficult, extremely time consuming and labor intensive. In response, a number of methods and equipment designs have been developed for crystallizing proteins (see, for example, U.S. Pat. No. 5,961,934, issued Oct. 5, 1999; U.S. Pat. No. 5,643,540, issued Jul. 1, 1997; U.S. Pat. No. 5,597,457, issued Jan. 28, 1997; U.S. Pat. No. 5,419,278, issued May 30, 1995; and U.S. Pat. No. 5,096,676, issued Mar. 17, 1992, having methods for forming protein crystals suitable for crystallography) and for streamlining the effort required to identify and reproduce appropriate conditions for crystallization of proteins (see, for example, U.S. Pat. No. 5,641,681, issued Jun. 24, 1997, showing a method for obtaining conditions for growth of high quality protein crystals). A number of physical and chemical factors can impact upon protein formation and crystal growth, so that, for example, it has been proposed that protein crystals be produced in a satellite in earth orbit having zero gravity.

Thus, there is a need for a less time consuming and expensive method for determining the surface topology of proteins, to benefit medical and biological research and facilitate the development of new medications.

Furthermore, there is a need for a means to quickly identify potential binding sites on specific proteins. In many pharmaceutical and diagnostic commercial applications, only potential binding sites on the surface of a protein, rather than a detailed model of all atomic coordinates, are of interest. Identifying binding sites by current methods requires sophisticated analyses of the three-dimensional structure of the protein involving complex numerical modeling. Thus, a less expensive and more direct method for determining potential protein-binding sites would be of economic value.

There is also a need for reliable diagnostic devices to diagnose individuals who are infected, for example, by a new or rapidly mutating pathogen, such as human immunodeficiency virus (HIV), influenza virus, or malaria, or other disease states that have evaded simple diagnostic tests, such as certain forms of cancer or pre-cancerous conditions.

SUMMARY

In one embodiment, the invention provides a method for discovering protein adsorption sites on a surface, comprising: providing a test surface having a surface topology comprised of a random distribution of randomly shaped features of a size from about $10^{-10}$ meters (one Angstrom) to about $10^{-8}$ meters (10 nanometers) in width, height, depth and spacing; exposing the test surface to a solution of a substantially purified protein, the solution remaining in contact with the surface sufficiently long to enable protein molecules to adsorb to adsorption sites; removing the solution with unadsorbed protein molecules from the test surface; and identifying the protein adsorption sites by detecting the presence of adsorbed protein molecules, to locate protein molecules adsorbed to the test surface.

A related method further includes removing the protein molecules adsorbed to the test surface, and measuring the surface topology of the identified adsorption site.

In accordance with a related embodiment, the method further comprises analyzing statistically the surface topology of a statistically significant number of identified adsorption sites to determine a most probable adsorption site topology. Measuring the surface topology further comprises using one or more of the group consisting of: a microcantilever, an atomic force microscope, a scanning tunneling microscope, a magnetic resonance force microscope, a thermomechanical atomic force microscope, a multi-tip atomic force microscope, and microparticles coupled to protein molecules adsorbed to the test surface. The method in various embodiments further comprises storing the most probable adsorption site topology in a computer database.

Another related method includes detecting the presence of adsorbed protein molecules using a microcantilever. Yet another related method includes detecting the presence of adsorbed protein molecules using, for example: an atomic force microscope; a scanning tunneling microscope; a magnetic resonance force microscope; a thermomechanical atomic force microscope; is a multi-tip atomic force microscope; or coupling a microparticle to protein molecules adsorbed to the test surface.

Another related method includes using a plurality of different surface coatings deposited on the test surface, each coating having a characteristic resiliency, and further comprising determining which of said surface coatings is deposited on the identified adsorption sites by measuring the resiliency of the deposited surface coatings using an atomic force microscope.

Another related method includes using a plurality of different surface coatings deposited on the test surface, each coating having a characteristic conductivity, and further comprising determining which of the surface coatings is deposited on the identified adsorption sites by measuring the conductivity of the deposited surface coatings using a conducting atomic force microscope.

Another related method includes providing a test surface wherein the features are not randomly distributed, and the features have a width, a height, a depth and a spacing in an identical pattern distributed regularly on the test surface.

In another embodiment, the present invention provides a method for determining a topology of protein binding sites, comprising: providing a test surface having a surface topology having a random distribution of randomly shaped features of a size from about $10^{-10}$ meters to about $10^{-8}$ meters in width, height, depth and spacing; depositing a solution containing substantially a single type of protein molecules on the test surface, and permitting the solution to remain sufficiently long to enable the protein molecules to adsorb to protein binding sites on the test surface; removing unadsorbed proteins from the test surface; using an atomic force microscope for identifying a location of the adsorbed protein molecules on the test surface; and determining the topology that is complementary to the surface topology measurements of the identified adsorption sites. This method can further comprise, prior to depositing a solution of proteins on the test surface, using an atomic force microscope to obtain a plurality of surface topology measurements of the test surface, and recording the surface topology measurements in a computer database. This method can also further comprise analyzing a statistically significant number of the surface topology measurements of the identified adsorption sites, to determine a most probable adsorption site topology and a most probable complementary protein surface topology of the single type of protein.

In another embodiment, the present invention provides a method for determining attachment areas on a surface of a species of a micro-organism, comprising: providing a test surface having a surface topology comprised of a random distribution of randomly shaped features of a size from about $10^{-10}$ meters to about $10^{-8}$ meters in width, height, depth and spacing; depositing a sample containing a plurality of units of the micro-organism on the test surface and permitting the sample to remain in contact with the test surface sufficiently long to enable surface proteins on the micro-organism to adsorb to areas on the test surface; removing unadsorbed units of the micro-organism from the test surface; and identifying the location of attachment areas on the test surface by using a microscope by locating micro-organisms adsorbed to the test surface. The method includes an embodiment wherein the units of the micro-organism are selected from the group of virions, bacterial cells and spores.

In another embodiment, the invention provides a method for determining a topology of potential protein binding sites for a surface of an envelope of a pathogen, comprising: disrupting the pathogen, removing soluble components, and solubilizing envelope proteins of the pathogen, to obtain a sample of surface proteins of the pathogen; providing a test surface having a surface topology comprised of a random distribution of randomly shaped features of a size from about $10^{-10}$ meters to about $10^{-8}$ meters in width, height, depth and spacing; depositing the sample of surface proteins on the test surface and permitting the sample to remain in contact with the surface sufficiently long to enable proteins to adsorb to features on the test surface; removing unadsorbed proteins from the test surface; and identifying sites on the test surface by detecting the locations of adsorbed pathogen surface proteins, to locate sites on the test surface for adsorption of proteins the pathogen envelope.

In accordance with related embodiments, the method includes: identifying the adsorption sites with an atomic force microscope, to obtain surface topology measurements of the identified adsorption sites; analyzing statistically the surface topology measurements of a statistically significant number of the identified adsorption sites, to determine a most probable adsorption site topology; storing the most probable adsorption site topology in a computer database; determining a complementary topology to the most probable adsorption site topology; or storing the complementary topology in a computer database. In accordance with a related embodiment, the pathogen is a virus or a bacterium. Further, the absorbed surface proteins can be further characterized by eluting from the test surface, for example, wherein eluting protein from the test surface is characterizing the protein molecule by laser desorbing and analyzing a time-of-flight characteristic, for example, wherein analyzing the time-of-flight characteristic comprises obtaining a molecular weight. Obtaining the molecular weight further comprises comparing the molecular weight to protein sequence data predicted from a sequence of a nucleic acid of the pathogen.

In yet another embodiment, the invention provides a method for rapidly developing a diagnostic device for a disease, comprising: obtaining a first set of biological samples from each of a statistically significant number of individuals having a disease, and a second set of biological samples from each of a statistically significant number of disease-free individuals; providing a test surface having a random distribution of randomly shaped features of a size from about $10^{-10}$ meters to about $10^{-8}$ meters in width, height, depth and spacing; depositing each of first set of the biological samples on the test surface, and permitting each sample to remain sufficiently long to enable proteins from each of the first set to adsorb to adsorption sites; removing unadsorbed proteins from the test surface; identifying adsorption sites on the surface from each of the samples of the first set by detecting the presence of an adsorbed protein, to locate proteins adsorbed to the test surface; repeating the method for each of the samples from each of the second set; and identifying a pattern of protein adsorption sites that is different in samples of the first set having the disease compared to samples of the second set lacking the disease.

Accordingly, the disease can be a type of cancer or a precancerous condition; further, the disease can be infection by a human immunodeficiency virus. In related embodiments, the invention provides a diagnostic device having a protein adsorption pattern discovered by any of these methods, for example, a diagnostic device replicating a surface topology of a protein adsorption site, using test surface topology measurements obtained by such a method. Further, related embodiments include a composition which is a protein associated with a disease, the protein being identified using any of the related embodiments of the methods.

In yet another embodiment, the invention provides a method for determining potential molecular attachment areas on a surface of a pathogen comprising: providing a test surface having a surface topology comprised of a random distribution of randomly shaped features of a size from about $10^{-10}$ meters to about $10^{-8}$ meters in width, height, depth and spacing; depositing a solution containing a preparation of units of the pathogen on said test surface and permitting said solution to remain sufficiently long to enable surface proteins on the pathogen to adsorb to adsorption sites on the test surface; removing unadsorbed pathogen from the test surface; and identifying adsorption sites on said test surface by using a microscope to locate units of the pathogen adsorbed to said test surface. For example, the units of the pathogen are virions or bacteria.

In yet another embodiment, the invention provides a diagnostic device, comprising: a test surface having a surface topology comprised of a random distribution of randomly shaped features of a size from about $10^{-10}$ meters to about $10^{-8}$ meters in width, height, depth and spacing; a pattern of protein adsorption sites of known specificity on the test surface; and a reader capable of detecting proteins adsorbed to the pattern protein adsorption sites of known specificity. A related embodiment is provided, further comprising a fluidics cell, the fluidics cell having a fluid inlet, a fluid outlet, and a wall structure coupled to the test surface. For example, the fluid inlet and the fluid outlet are micropipettes coupled to the wall structure.

In yet another embodiment, the invention provides a protein assay apparatus, comprising: an atomic force microscope, the atomic force microscope having a multi-tip microcantilever array sensor; a positioning table coupled to the atomic force microscope and configured to position a sample for inspection by the multi-tip microcantilever array; and a test surface coupled to the positioning table, the test surface having a surface topology comprised of a random distribution of randomly shaped features of a size from about $10^{-10}$ meters to about $10^{-8}$ meters in width, height, depth and spacing. In accordance with related embodiments, the protein assay apparatus further comprise a fluidics cell, the fluidics cell having a fluid inlet, a fluid outlet, and a wall structure coupled to the test surface. The fluid inlet and the fluid outlet can be micropipettes coupled to the wall structure; the positioning table can be a turntable, for example, the turntable is a miniature computer drive platform. The protein assay apparatus can further comprise a fluidics cell coupled to the test surface, the fluidics cell having a fluid inlet and a fluid outlet and comprising a wall structure coupled to the test surface.

DETAILED DESCRIPTION OF SPECIFIC EMBODIMENTS

Figure 1:
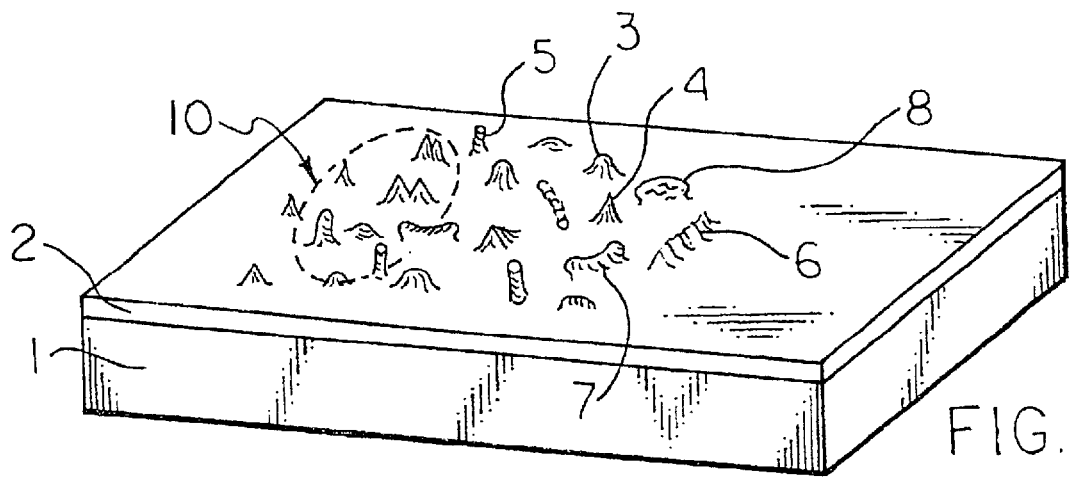
FIG. 1 is a perspective diagrammatic view of a test surface with randomly shaped nanostructures randomly distributed on one side.

Protein surface topology information is useful in some applications to implement methods and devices for detecting specific proteins and nucleic acid chains (see, U.S. Pat. No. 6,123,819, issued Sep. 26, 2000). Nanometer-scale electrodes (nanoelectrodes) formed on the surface of a substrate, such as silicon, at specific locations and with specific heights relative to the substrate in a combination of a small number of the nanoelectrodes, can precisely match the folds and bumps of the protein's surface topology. Targeted proteins will preferentially adsorb to the nanoelectrodes in a lock-and-key manner, held in place by van der Waals forces. Proteins having surfaces that do not complement specific patterns presented by the nanoelectrodes will not adsorb to the substrate, and are eliminated by being washed away. This method of immobilizing and detecting target proteins eliminates the need for time-consuming chemical and electrophoretic protein detection processes in use today.

Fabrication methods are available for building nanoelectrode structures in precise locations and dimensions needed to create such specific adsorption sites. Such fabrication methods include using a scanning tunneling microscope (STM) to place small atom clusters on the substrate. A detailed understanding of the topology of the protein is required in order to fabricate the specific set of nanoelectrodes, in the proper positions and with the necessary dimensions, to create a matching nanoelectrode cluster adsorption site. Thus, there is a need for a method to rapidly and economically determine the configurations of nanoelectrodes that will adsorb selected particular proteins.

Embodiments of this invention include methods for discovering protein adsorption sites on a test surface, and determining from such results information on protein surface topology, detecting unknown proteins, and developing new diagnostic devices and diagnostic device apparatuses. These methods use a test surface that features randomly configured nanometer-scale structures (nanostructures or nanoelectrodes). A basic method comprises providing a suitable test surface, depositing a solution of target proteins on the test surface, permitting sufficient time to elapse so that protein molecules encounter and adsorb to sites on the test surface, removing unadsorbed protein molecules from the surface, and inspecting the surface to identify sites where protein adsorption has occurred. Information on the surface topology of the protein, as well as topographic information useful for fabricating adsorption sites (such as for designing attachment molecules or mimetics for new drugs), are obtained by mapping each adsorption site with an atomic force microscope (AFM). The AFM can be equipped with a microcantilever with an ultra fine tip, for example, a carbon nanotube tip, and additionally can be equipped with microcantilever tip positioning capabilities. For some embodiments, the AFM can have Angstrom level precision. The AFM can be customized also to have very low noise, due for example, to vibration or electrical noise, using components that can be custom made by the supplier (e.g., Molecular Imaging Corp., 9830 S. $51^{st}$St., Suite A124, Phoenix, Ariz. 85044). By creating greater than about $10^9$ random topology features on a test surface, and permitting given target proteins to randomly encounter and adsorb to complementary features, the method bypasses the need to know a detailed structure of a protein in order to fabricate the adsorption sites.

Inventions embodied herein include new methods and diagnostic devices for identifying protein binding sites, identifying physical structures (e.g., a particular cluster of nanoelectrodes) that cause a protein to adsorb to a surface, and determining as defined by the nanoelectric cluster the surface topology of a given protein. By not relying upon X-ray crystallography, this invention eliminates the need for growing protein crystals and the expense and effort associated therewith. Embodiments of this invention further include methods for manufacturing a protein detection surface suitable for detecting the presence both of known proteins, and of discovering unknown proteins, as well as providing diagnostic devices for a given disease or diseases. An embodiment of the invention also enables the deconvolution of adsorption data from the test surface into three-dimensional data describing the surface structure of a given protein. A method and an apparatus for quickly developing a diagnostic device for a disease even if the disease etiology or pathogen structure are unknown or not well understood, are also provided.

Accordingly, an embodiment of the inventions provided herein is a diagnostic device and a new method for discovering potential binding sites of a protein on a specially prepared test surface, and deducing the surface topology of the protein from topology information obtained from the test surface protein adsorption sites. Also provided is a method for rapidly discovering unknown proteins, particularly those associated with a given disease, for developing a diagnostic device for a disease, and for providing information on the proteins' surface topology that may be used to develop new drugs and diagnostic devices for a disease.

A test surface is prepared that features a random distribution of nanometer-scale structures (e.g. spikes, bumps, columns, ridges, valleys and dimples) extending from the surface or substrate a distance of from about $10^{-10}$ meters to about $10^{-8}$ meters, having a width or diameter of about $10^{-10}$ meters to about $10^{-8}$ meters, and spaced about $10^{-8}$ meters to about $10^{-10}$ meters apart on average. At this size scale, billions of such nanostructures can be positioned on a one-centimeter square chip of silicon substrate. Suitable surfaces may be commonly encountered in nature or during material fabrication or by modification of industrial processes. The target protein, for which binding site information is desired, is introduced onto the test surface, and then the surface is washed to remove unadsorbed proteins. An AFM, or other suitable means for detecting an individual adsorbed protein, is used to find the plurality of proteins adsorbed to the test surface, and to identify the precise location on the test surface where adsorption occurs. Finally, an AFM is used to measure the precise locations and heights of the nanostructures that cause adsorption to occur.

Adsorption site topographic information is stored in a computer database to create a useful library of information for use in protein identification, protein purification, diagnostic device development, pharmaceutical development and basic research. Using the physical dimensions of the adsorption site on the test surface, the complementary topology of the protein surface is deduced. Protein surface topology information is stored in a computer database to create a useful library of information for use in pharmaceutical development, diagnostic device development and basic research. Since a protein may have binding sites on a number of areas of its surface, its overall surface topology can be deduced by combining topology information on all adsorption sites discovered on a test sample of a pure protein. Such whole protein surface topology information is stored in a computer database to create a useful library of data for use in pharmaceutical development, diagnostic device development and basic research.

Unknown proteins associated with a given disease are discovered by using the invention method for a statistically significant number of individuals with the disease and a statistically significant number of individuals without the disease, detecting and recording the pattern of protein adsorption sites on a particular test surface for each individual, determining the most probable protein adsorption site patterns for diseased and nondiseased individuals, and subtracting the nondiseased pattern from the diseased pattern to reveal the disease-specific protein adsorption site pattern for the test surface. With the disease-specific pattern identified, the test surface washed to remove bound proteins and can be reused, or the surface can be replicated and used as a component of a diagnostic device for the specific disease by coupling it with a reader that can detect proteins adsorbed on the surface and recognize the disease-specific adsorption pattern. The test surface is further used to identify the topologies of the proteins surface for applications in pharmaceutical development.

In one embodiment of this invention, the topology information (i.e. nanostructure height, width, and relative positions) for a test surface adsorption site is translated directly into fabrication instructions for placing nanoelectrodes on protein detector chips. Such fabrication instructions for placing nanoelectrodes on protein detector chips is stored in a computer database for use in diagnostic device development and fabrication, as well as for general research purposes.

In another embodiment of this invention, the relative affinity of a protein for a particular adsorption site is determined by detecting the presence of proteins after cycles of rinsing, each cycle using a buffer of increasing stringency in comparison to the previous buffer, thereby determining which of the discovered adsorption sites binds the target protein with greater affinity, the adsorption sites each having a particular topology. The term "increasing stringency" refers to use of characteristics of a series of washes using buffers having increasingly high or low pH, or increasingly high or low ionic strength, or presence of one or more detergents at increasing concentrations, as well as the washes being preformed at increasingly high temperature. These characteristics can be experimentally varied to denature and therefore elute proteins sequentially as a function of relative affinity from the surface, so that a final wash removes proteins having greatest affinity to a particular adsorption site. Use of any one or more of these characteristics, alone or in combination at an extreme end of a range, may not be necessary, as a local region of denaturation of an adsorbed protein can cause elution of a protein of interest from the adsorption site. Once conditions are established for elution of a particular protein, the procedures for washing and elution can be preformed in a few steps, as can readily be determined by one of ordinary skill in the art of protein purification. Information on the relative adsorption affinity of a protein to particular adsorption site topologies is stored in a computer database for use in diagnostic device development, pharmaceutical development and general research.

In another embodiment of this invention, a protein detection surface is created by using the adsorption site discovery method to map on a random test surface all the adsorption locations for each of a number of known proteins, and then replicating the surface to produce a line of detection surfaces suitable for use with a reader that can read the position of all adsorbed proteins.

An AFM detects atomic-scale features based upon the force or the atomic interaction between the features present against a very fine tip of the AFM that is mounted at the end of a microcantilever, and positioned so that the tip merely touches or comes very close to the surface of these features. A microcantilever is a thin bar of material, such as silicon, having dimensions, for example, of about 30 micrometers to about 400 micrometers in length, of about 10 micrometers to about 50 micrometers in width, and of about 0.3 micrometers to about 12 micrometers in thickness, generally fabricated out of semiconductor materials using microfabrication processes developed for microchip manufacturing. The tip of the microcantilever can be much smaller, for example, as small as a few atoms across. A number of methods for producing microcantilevers with ultra fine tips have been demonstrated. Atomic force microscopes, and the microcantilevers used therein, are well known (see, for example, U.S. Pat. No. 4,724,318 which issued Feb. 9, 1988).

FIG. 1 shows a detail of a test surface used in this method. A suitable test surface comprises a smooth substrate 1 of a material suitable for precision fabrication processes, such as silicon, silicon oxide, silicon nitride, gallium arsenide, graphite, mica, gold or other metal. On the surface of the substrate is deposited a coating 2 of random topology features, including bumps 3, spikes 4, columns 5, ridges 6, valleys 7, dimples 8 and other shapes that are from about $10^{-10}$ meters to about $10^{-8}$ meters in width and height or depth and spacing, with a significant fraction of the topology features having a width and height or depth, for example, of about 2 Angstroms to about 5 nanometers. A suitable density of such topology features will result in an average spacing of about 2 Angstroms to about 5 nanometers, with a random distribution of spacing and positional orientations. A second coating or surface treatment may be applied to the topology features, such as gold plating to reduce chemical reactivity, hydride or oxide to create a desired surface electron motility or other treatment to affect the surface charge exhibited on the topology features, or to stabilize the surface. An adsorption site 10, which is indicated with a dashed outline, comprises a cluster of nanostructures with the proper size, shape, geometry and spacing to exactly complement the surface topology of a protein. It is anticipated that adsorption sites for a particular protein may consist of many alternative configurations of nanostructures and surface areas, each of which provide a profile to a protein that complements a portion of the protein's surface topology. In one embodiment, the features are in clusters that are some distance from each other on an otherwise flat surface. See, for example, First, P. et al., Phys. Rev. Lett. 63(13): 1416–1419 (1989).

Figure 2:
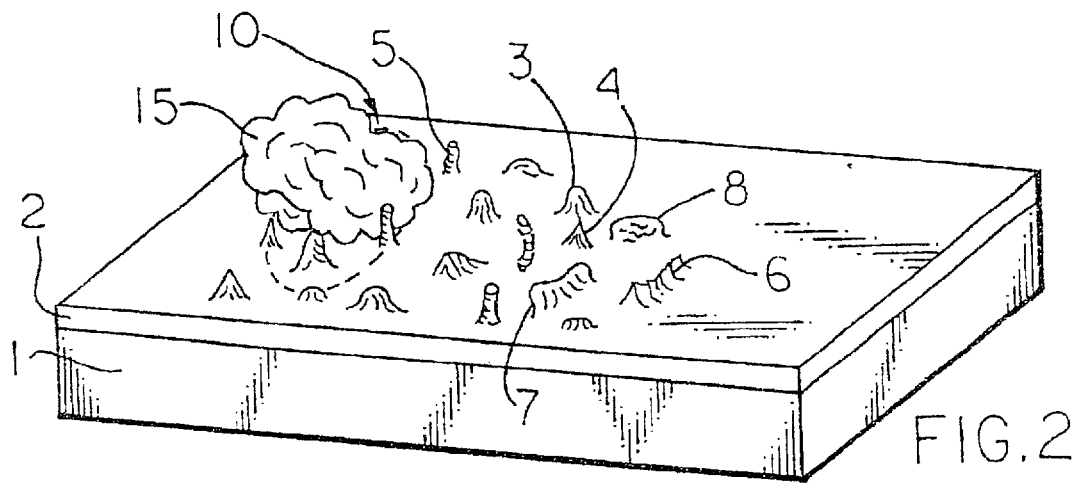
FIG. 2 is a perspective diagrammatic view of a test surface with a protein adhering to a adsorption site on the test sample.

FIG. 2 shows a protein 15 which is adsorbed to an adsorption site 10 when the protein encounters a coating 2 area of the test surface having a topology comprised of bumps 3, spikes 4, columns 5, ridges 6, valleys 7, dimples 8 and other shapes that complement the protein's surface topology. A substrate 1 underlies the coating 2. Van der Waals forces between the surface topology features and the protein surface attract the protein and cause the protein to adsorb to the adsorption site until other forces dislodge it or the protein denatures. Proteins will not adsorb tightly to the surface where there is no surface complementarity, and therefore can be easily washed away. Thus, adsorption sites for a particular protein can be discovered on a test surface by permitting a solution of the target proteins to interact with the surface long enough for protein molecules to randomly encounter and adsorb to complementary topology sites, after which the unadsorbed solution can be gently rinsed off leaving only proteins adsorbed to adsorption sites.

After the protein solution has interacted with the test surface and unadsorbed proteins have been washed away, the test surface is inspected using an AFM or other suitable means for detecting adsorbed proteins to locate the position of proteins adsorbed to the test surface. In addition to using an AFM or scanning tunneling microscope (STM) to locate adsorbed proteins, the proteins may be made opaque or tagged with microparticles by coupling to the proteins specially tagged antibodies or dye molecules so the protein-microparticle complexes can be located using optical, electrical or magnetic readers.

Figure 3:
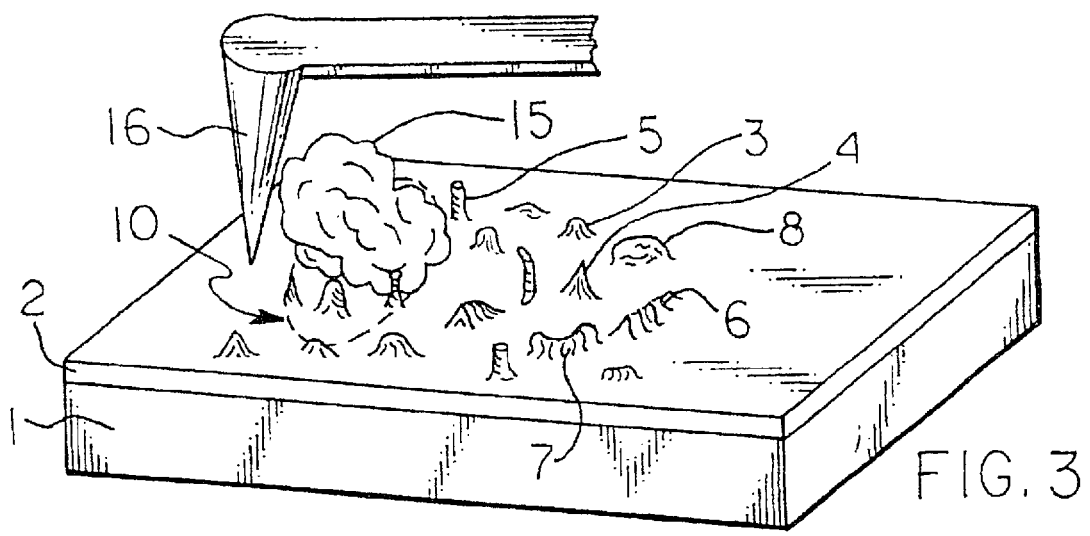
FIG. 3 is a perspective diagrammatic view of a test surface and the probe of an atomic force microscope (AFM), to locate proteins adhering to the test surface.

FIG. 3 illustrates the detection with an AFM tip 16 of a protein 15 adsorbed to the coating 2 on the substrate 1 at an adsorption site 10 that is formed of bumps 3, spikes 4, columns 5, ridges 6, valleys 7, dimples 8 and other shapes in the coating 2. When an AFM is used to detect adsorbed proteins, the AFM tip 16 scans across the test surface coating 2 until it detects the raised profile of a protein molecule 15. When an adsorbed protein is located, the AFM tip 16 is used to accurately locate the boundary of the protein 15, which defines the boundary and coordinates of the adsorption site 10, with respect to a known or defined reference point on the test surface. Once the protein boundary is identified, the AFM continues scanning the test surface to locate other adsorbed proteins. This process is continued until a sufficient number of protein adsorption sites have been identified to enable obtaining statistically significant results, so that the method of adsorbing proteins to the surface, washing away unadsorbed proteins, and scanning for adsorbed proteins may be re-iterated to obtain sufficient data to inspect an entire test surface.

An AFM is one example of a variety of devices for detecting adsorbed proteins on the test surface. Another device for detecting proteins adsorbed on the test surface is an STM, that has a tip (probe) similar in shape to the tip 16 shown in FIG. 3. Rather than contacting or approaching proximal to the protein as does an AFM, an STM detects the presence of a protein by the change in current conducted across the gap between the test surface and the tip 16. Another device for detecting adsorbed proteins on the test surface is a magnetic resonance force microscope (MRFM) that measures the change in magnetic resonance of the surface as a needle tip passes close to the surface. MRFM methods are shown by J. A. Sidles, et. al. "Magnetic Resonance Force Microscopy," Rev. Mod. Phys. 67, 249 (1995). An MRFM has a tip similar in shape to the tip 16 shown in FIG. 3. A technique for detecting adsorbed proteins include, for example, chemically attaching a microparticle or dye molecule to the adsorbed protein. Using a ferromagnetic microparticle bound to the protein molecules, a magnetic sensor such as a modified reader head from a computer disk drive, can detect proteins adsorbed on a test surface. A computer disk drive reader head also can be modified to include an AFM or silicon needle to rapidly scan the test surface. Another device for detecting adsorbed proteins is a sensitive optical sensor, such as a charged coupled device camera, capable of detecting a dye molecule bound to the protein. A laser or other illumination device can be used to excite the dye molecules. Methods to detect single molecules are known in the art. See, for example, Weiss, S., Science 283: 1676–1683 (1999).

Once adsorption sites are located, the proteins are removed by washing, for example, with a solution of higher or lower pH, salt concentration, or detergent concentration, or by exposure to heat, ultraviolet light or other method suitable for denaturing and removing proteins without affecting the test surface topology features.

Figure 4:
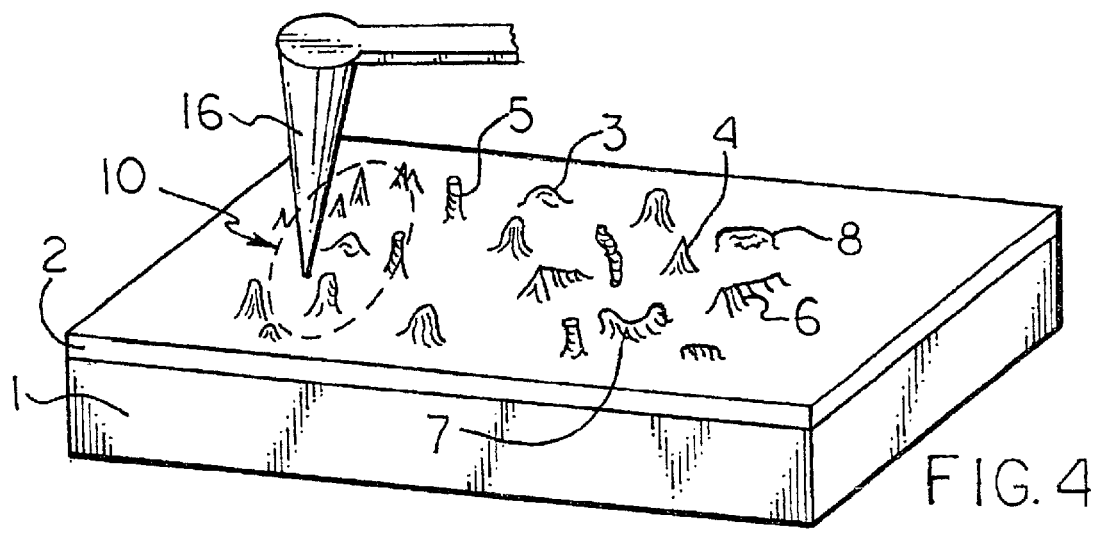
FIG. 4 is a perspective diagrammatic view of a test surface showing the use of an AFM to measure the geometry of a discovered protein adsorption site.

Referring to FIG. 4, the AFM 16 having an ultrafine tip can be used to map the topology of the adsorption site 10 in fine detail. Precise measurements of the height, width and spacing between the bumps 3, spikes 4, columns 5, ridges 6, valleys 7, dimples 8 and other shape features in the coating 2 on substrate 1 are obtained, as well as the precise location (, e.g., X-Y coordinates) of the adsorption site on the surface. This method is repeated for each adsorption site that is identified on the test surface for a particular protein. Similarly, the three-dimensional shapes of non-adsorption sites can be mapped and stored in a computer database. Advances in AFM technology allow the ultraprecise positioning and repositioning of the tip to the same location coordinates.

Figure 5:
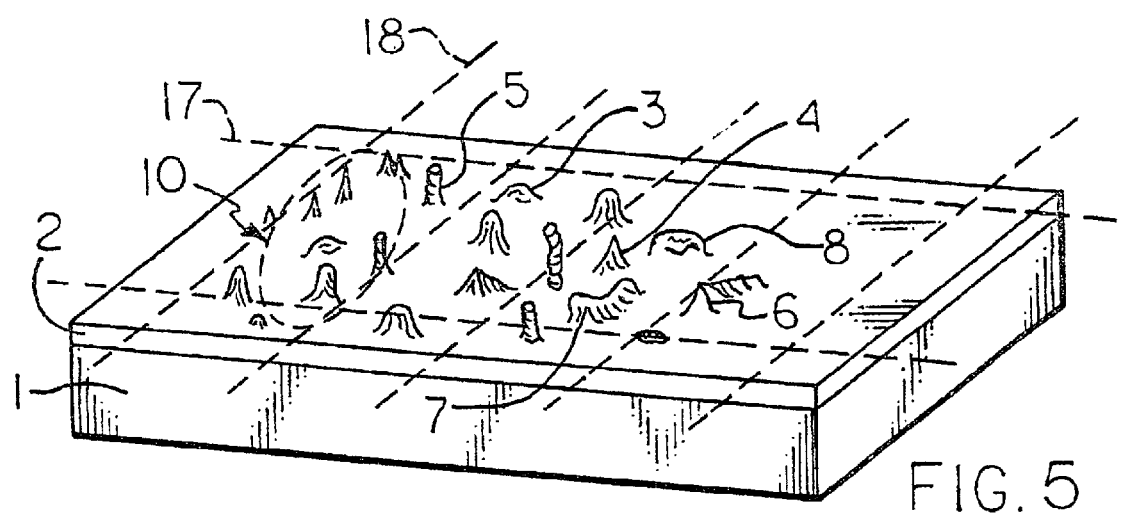
FIG. 5 is a diagrammatic view of a test surface showing a grid overlay for characterizing and storing the coordinates of the pattern of protein adsorption sites.

Referring to FIG. 5, the location on the test surface of adsorption sites can be mapped by using a physical or virtual coordinate grid that encompasses the active area of the test surface. Horizontal grid lines 17 and vertical grid lines 18 comprise a Cartesian coordinate system that can be created by a computer controlling an AFM, and then used again after adsorbing the proteins to the test surface, to specify the precise location of each adsorption site. The coordinate grid can be positioned with respect to fixed points or an axis provided on the test surface during fabrication, such as small dots of gold bonded to the surface. Alternatively, the coordinate grid can be aligned by the computer to unique features discovered on the test surface during inspection. Using a coordinate grid, the computer controlling the AFM records the grid coordinates of all of the bumps 3, spikes 4, columns 5, ridges 6, valleys 7, dimples 8 and other shapes in the coating 2 on substrate 1. The grid coordinates, along with the height, depth and width of each feature, are stored in a computer database for subsequent use and reference.

Figure 6:
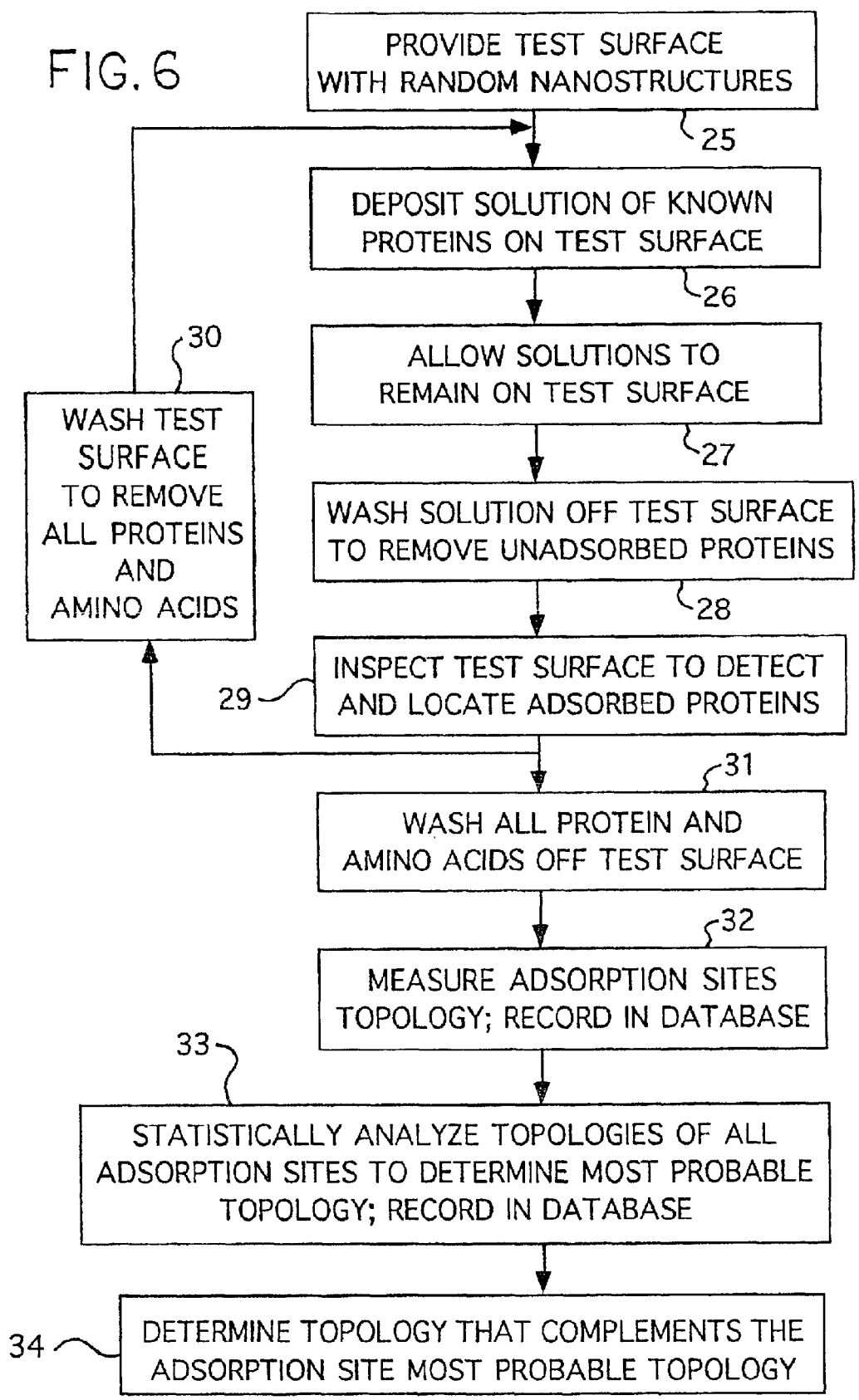
FIG. 6 is a block diagram of a method for discovering adsorption sites, determining the topology of such adsorption sites and deducing the surface topology of a protein.

FIG. 6 illustrates a process for determining the topology of an adsorption site on a test surface and inferring the protein surface topology which binds to that adsorption site. A suitable test surface is provided at 25. A solution of a known protein is deposited on the test surface in 26. The protein solution is permitted time to react with the test surface in 27. Unadsorbed proteins are washed from the surface in 28. The test surface is inspected with a means for detecting adsorbed proteins, such as an AFM, to identify adsorption sites, with the location of identified adsorption sites stored in a computer database in 29. If necessary, the test surface may be washed of all proteins in 30 so that 26 through 29 can be repeated. Proteins are then removed from the test surface in 31. Adsorption sites are inspected to measure their topology with the data recorded in a computer database in 32. After topology information has been gathered for numerous adsorption sites, the topology information is statistically analyzed to determine a most probable topology for the adsorption sites in 33. The complement to the most probable absorption site topology is determined, which corresponds to the topology of the surface of the protein in the region of adsorption, such protein surface topology information being stored in a computer database in 34.

Figure 7:
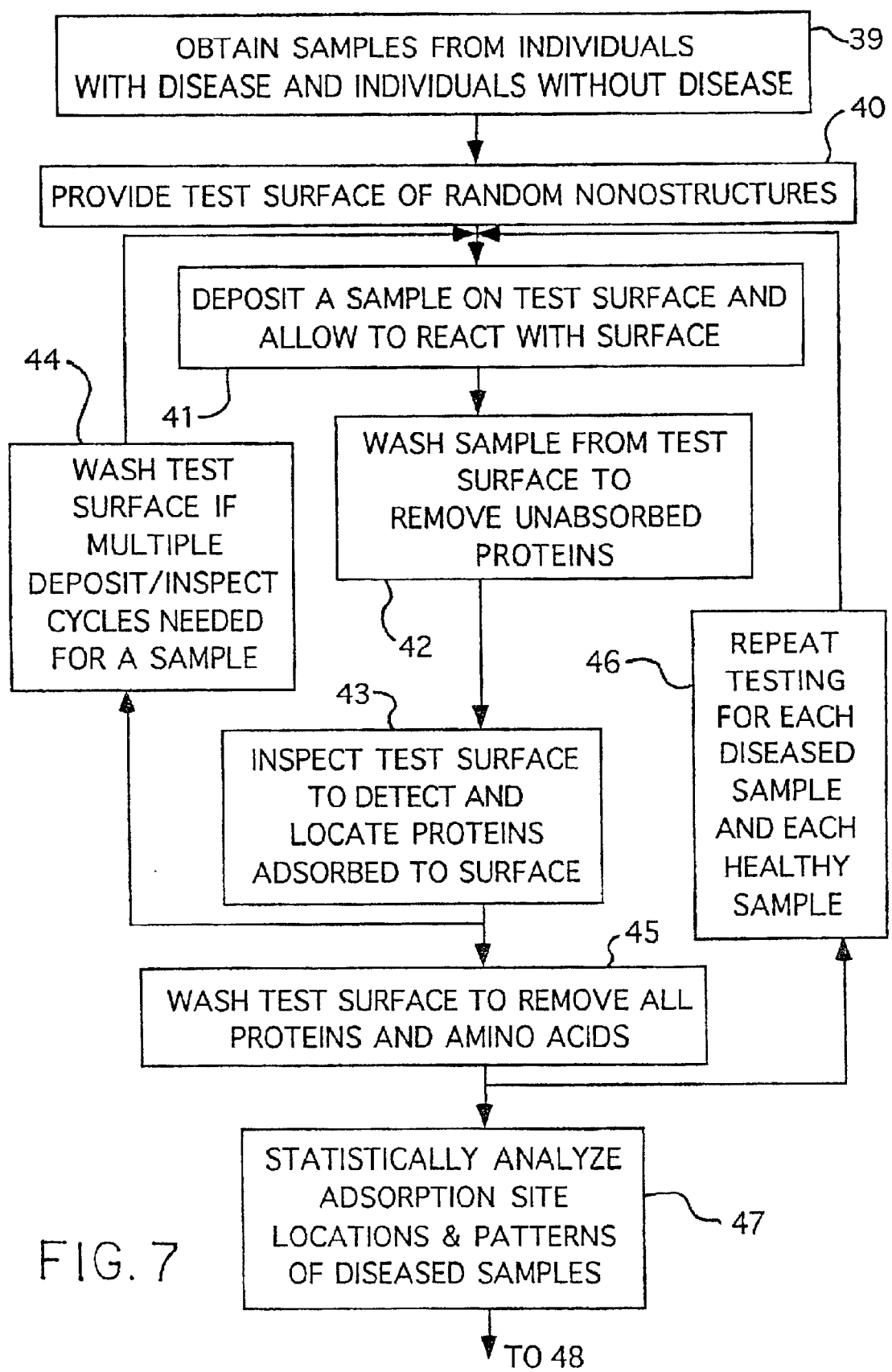
FIG. 7 is a block diagram of a method for rapidly developing a diagnostic device for a disease.
Figure 7:
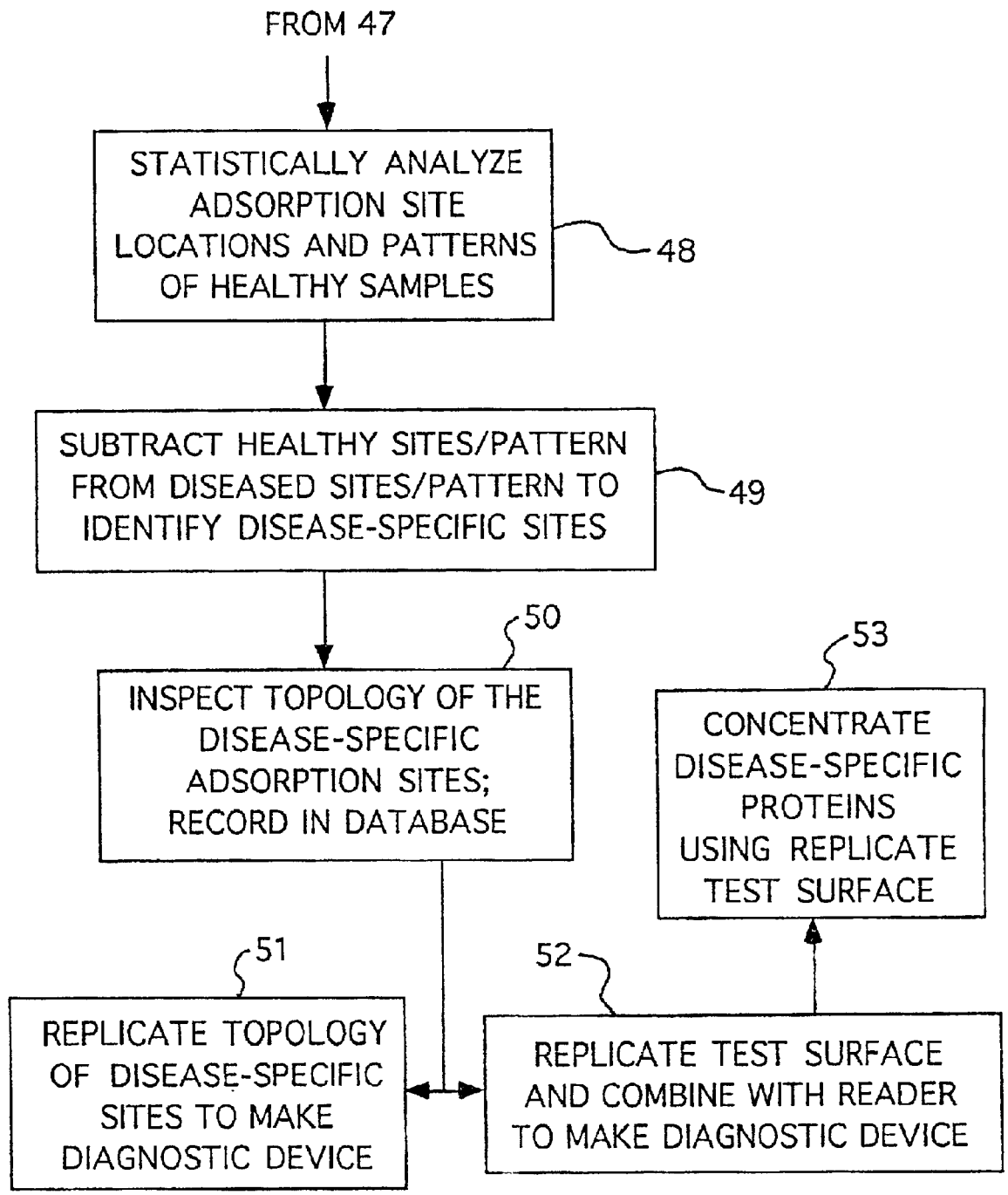

FIG. 7 illustrates a preferred process for creating a diagnostic device for diagnosis of a specific disease of a plant or animal species, for example, a disease of a human. Biological samples from a significant number of individuals having a given disease, and biological samples from a significant number of healthy individuals (i.e. free of the given disease), are obtained in 39. A suitable test surface is provided at 40. A biological sample from an individual is deposited on the test surface and permitted to remain on the test surface long enough for proteins to adsorb to adsorption sites in 41. Nonadsorbed proteins are washed from the test surface in 42. The test surface is inspected with a means for detecting adsorbed proteins, such as an AFM, to identify adsorption sites, and the location of each of the identified adsorption sites is stored in a computer database in 43. If necessary, the test surface may be washed of all proteins in 44 so that 41 through 43 can be repeated as necessary. All proteins are then removed from the test surface in 45 so 41 through 44, can be repeated for biological samples from a statistically significant number of individuals with a given disease and a statistically significant number of individuals free of the disease as shown in 46. Then, protein adsorption site position information is analyzed statistically to determine a most probable adsorption site location or pattern of adsorption for individuals having a particular disease in 47. Protein adsorption site position information is statistically analyzed to determine a most probable adsorption site locations or pattern for individuals free of the disease in 48.

The protein adsorption site location information or pattern from the disease-free samples is subtracted from the disease-specific protein adsorption site location information or pattern samples, to reveal the difference. The difference is the disease-specific protein adsorption site location information or pattern, which is recorded in a computer database in 49. The disease-specific adsorption sites are inspected with an AFM to obtain topology information, which is recorded in a computer database in 50. The disease-specific adsorption site topologies are replicated on new test surfaces to create diagnostic devices for the disease in 51.

Alternatively, the entire test surface is replicated and then combined with a reader capable of recognizing the locations or pattern of adsorption sites associated with the disease to create a diagnostic device for the disease in 52. Using a test surface comprising only replicated adsorption sites for a given type of protein, such proteins can be extracted and substantially enriched from a mixed solution for characterization and analysis, by allowing the solution to react with the replicated test surface, washing away unadsorbed proteins, and then washing the adsorbed proteins into a separate container or directly analyzing the proteins using a technique such as matrix assisted laser desorption/ionization time-of-flight (MALDI-TOF) mass spectroscopy, in 53.

Once the topology of the test surface adsorption sites is known, the topographic information can be used to reconstruct the protein's surface in the area of adsorption for given proteins of interest. Data on the height, width and spacing of surface features is combined with information on the surface electric fields of the test surface materials, to infer the surface topology of the protein. The surface topology of the protein where adsorption to the test surface occurs is valuable information, since it identifies the location and structure of potential molecular attachment areas on the particular protein that can be used to develop new treatments, drugs and diagnostic devices that exploit such attachment areas. Topographic data from all adsorption sites is then compared statistically to identify sites that correspond to similar portions of the surface of the protein, and to determine the most probable topology of an ideal surface adsorption site, and as its complement, the most probable configuration of the protein's binding sites. Finally, all most-probable protein binding site information is integrated (i.e. deconvoluted) to determine the entire surface topology of a given protein. This method can be used for any protein, known or as yet unidentified, for pure proteins, for substantially purified or isolated proteins, and for protein mixtures.

Figure 8:
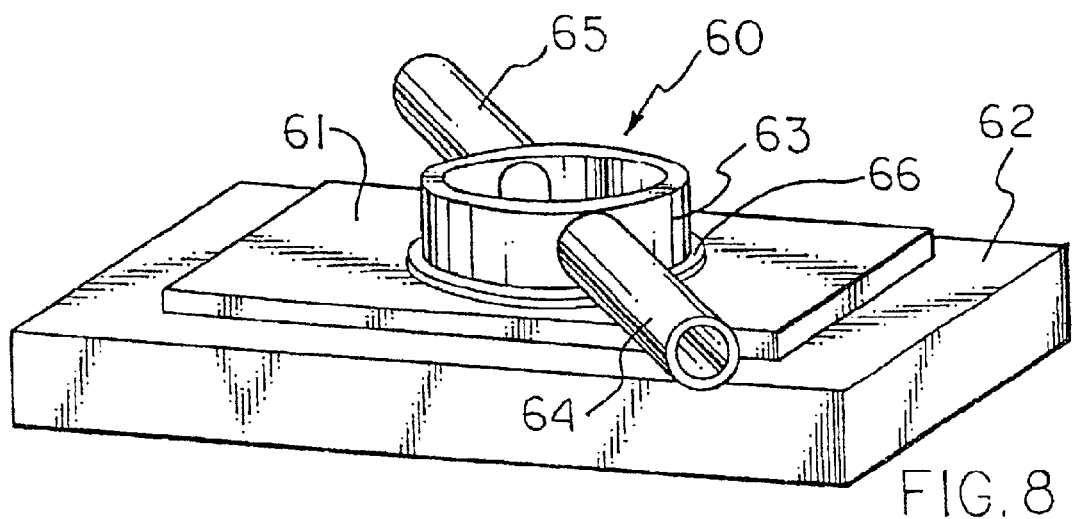
FIG. 8 is a perspective view of a fluidics cell positioned on a test surface on a positioning table.

FIG. 8 shows a preferred design for a fluidics cell 60 that will enable inspection of a large test surface without the need to remove the test surface from the AFM and without the problem of the test surface drying out. Specifically, the fluidics cell 60 is positioned on top of the test surface 61 which is attached to a positioning table 62. The fluidics cell 60 is comprised of a wall structure 63 through which a fluid inlet 64 and a fluid outlet 65 are provided. The wall structure 63 is of sufficient diameter to contain the sensor assembly of an AFM (not shown), and of sufficient height to maintain a fluid covering over the test surface 61. A rubber, polymer or similar material gasket 66 may be included on the bottom side of the wall structure 63 to provide a low-leakage seal with the test surface 61. Alternatively, the wall structure 63 may be glued, bonded, braised or similarly coupled to the test surface so the test surface 61 and fluidics cell 60 form a single unit. The positioning table 62 permits a large portion of the test surface to be inspected by an AFM without having to remove the AFM sensor from the surface. The fluid inlet 64 and fluid outlet 65 permit depositing solutions on the test surface and washing the test surface without having to remove the test surface from the AFM, thus permitting the AFM sensor to remain in a known position on the test surface 61 during deposition and washing steps.

Different designs for the fluidics cell 60, test surface 61 and positioning table 62 assemblage are possible and contemplated as part of this invention. For example, instead of mounting the wall structure 63 on top of the test surface 61, the test surface 61 may be positioned within the perimeter of the wall structure 63 which is directly mounted onto the positioning table 62. In such a configuration, the wall structure 63 may contain positioning aides (not shown) for the test surface 61 (e.g., pins or notches in the wall structure that match holes or protuberances provided on the test surface), and may be closed at the bottom or coupled to the turntable with a watertight bond, seal or attachment as a single unit.

Figure 9:
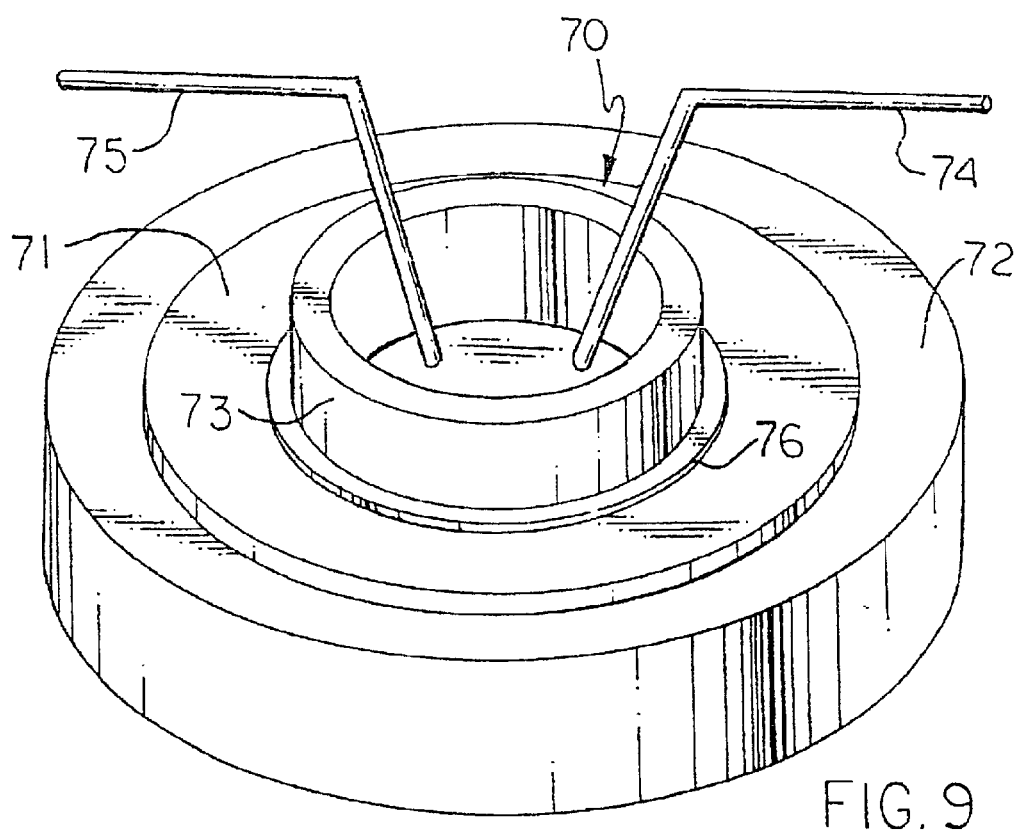
FIG. 9 is a perspective view of a fluidics cell positioned on a test surface on a turntable.

FIG. 9 shows a preferred design for a fluidics cell 70 configured for a turntable type of positioning table. Specifically, the fluidics cell 70 is positioned on top of the test surface 71 which is attached to a turntable 72. The fluidics cell 70 is comprised of a wall structure 73 which is of sufficient diameter to contain the sensor assembly of an AFM, and of sufficient height to maintain a fluid covering over the test surface 71. A fluid inlet 74 and a fluid outlet 75 are provided from above to enable fluids to be added to and withdrawn from the fluidic cell 70 while it turns on the turntable 72. A rubber, polymer or similar material gasket 76 may be included on the bottom side of the wall structure 73 to provide a low-leakage seal with the test surface 71. Alternatively, the wall structure 73 may be glued, bonded, braised or similarly coupled to the test surface so the test surface 71 and fluidics cell 70 form a single unit.

A turntable 72 permits the AFM sensor to scan a large area of the test surface without having to remove the test surface from the AFM, and with a simpler (i.e. single dimensional) positioning mechanism. Different designs for the fluidics cell, test surface and turntable assemblage are possible and contemplated as part of this invention. For example, instead of mounting the wall structure 73 on top of the test surface 71, the test surface 71 may be positioned within the perimeter of the wall structure 73 which is directly mounted onto the turntable 72. In such a configuration, the wall structure 73 may contain positioning aides for the test surface 71 (e.g., pins or notches in the wall structure that match holes or protuberances provided on the test surface), and may be closed at the bottom or coupled to the turntable with a water-tight bond, seal or attachment as a single unit.

A suitable test surface with its coating of random topology features may be fabricated by a number of processes, including etching, atomic sputtering, molecular sputtering, molecular beam epitaxy, random placement of nanostructures, sputtering of nanostructures, and atomic placement with a STM. Since the ideal adsorption site topology may be unknown, it is important that the coating deposition process be as random as possible in terms of structure, size, orientation and spacing.

U.S. Pat. No. 5,316,979, issued May 31, 1994, shows that anodic etching such as with phosphoric acid will create a near-random structure of pores and peaks on a silicon surface. U.S. Pat. No. 5,316,979 shows methods for fabricating submicron structures in silicon by controlled anodic etching. If the duration of etching is short, such as a minute or less, the depth of the resulting pores is kept shallow enough to achieve the topology feature size ranges within the necessary range of about $10^{-10}$ meters to about $10^{-8}$ meters.

A related method of fabricating the test surface modifies well-known semiconductor fabrication techniques to create a random distribution of pyramids. U.S. Pat. No. 4,513,308, issued Apr. 23, 1985, shows a method for fabricating pyramid-shaped structures on a semiconductor substrate. In such a process, a generally planar semiconductor substrate is oxidized to a depth of about 10 nanometers to create an oxide layer of $SiO_2$, after which a thin photoresist layer is coated on the oxide layer as is well known in the art. The photoresist layer is then exposed using short wavelength electromagnetic radiation or electrons in a random pattern. The random pattern may be created from a mask of randomly sized and spaced dots, or by directing the electron beam in a completely random pattern using a computer to orient the electron beam based upon the output of a random number generator. Next, the photoresist is developed, resulting in a random pattern of photoresist islands. The surface is then etched using known methods that preferentially remove the $SiO_2$ before the photoresist. Finally, the photoresist is removed to reveal randomly spaced pyramids. By controlling the photoresist and etching processes, pyramids of the desired size and shape can be produced.

Another suitable method of fabricating the test surface is atomic sputtering, under conditions and with fixtures to ensure that a random pattern of deposition is achieved. For example, glancing angle deposition methods have been described by Robbie, et. al. in *Thin films with nanometer-scale pillar microstructure*, Journal of Materials Research 14 (July 1999):3158, which produce nanometer-scale structures. By modifying the process disclosed by Robbie to enable random depositions of structures, such as rotating the surface in a chaotic pattern during deposition, and keeping the time of deposition short, structures of the size and random distribution required may be produced.

Another method for fabricating test surfaces involves sputtering of nanometer-scale particles onto the test surface substrate. Sputtering nanometer-scale rods or spheres of a metal, (such as gold), carbon (such as carbon nanotubes and fullerine spheres), or other material onto the substrate will result in a surface topology that retains aspects of the rod or sphere shapes, as well as the disordered surface of bumps and grooves that results from the random orientation and packing of the microparticles on the substrate.

Yet another method for fabricating test surfaces involves the use of an STM to deposit small clusters of atoms in specific locations selected in a random manner. The use of scanning tunneling microscopes to fabricate nanometer-scale structures on smooth surfaces was described by Kolb, et. al. in *Nanofabrication of Small Copper Clusters on Gold*(111) *Electrodes by a Scanning Tunneling Microscope*, Science, Vol. 275, 1097–99, Feb. 21, 1997. Since the STM operation is computer controlled, the deposition pattern can be controlled by a random number generator to create a random pattern of deposition sizes and spacing.

Suitable test surfaces may also be obtained from materials, natural processes and surface fabrication methods (including one or more of fractionation, purification or chemical modification) that create nanometer-scale surface features. Examples of such surfaces contemplated in this invention include oxidized metallic surfaces, mica, metallic and ceramic surfaces that have been polished to a less-than-mirror-quality surface using a fine grain abrasive, and rupture or fracture surfaces of materials such as plastics, glasses, naturally occuring materials, ceramics, semiconductors, carbides, metals and metal oxides.

Since protein adsorption may also depend upon the electronic field of the surface features, a random distribution of different surface coatings may be included on the test surface. Different surface coatings will exhibit different charge moieties that may complement the charged chemical moieties of various regions of the target protein. Random distributions of test surface coatings may be achieved by sputtering while rotating the test surface in a chaotic manner or by sputtering through a mask featuring holes of random size and random positional distribution. Candidate surface coatings include oxides, nitrides, hydrides, carboxylates, sulfonates, phosphates, phosphonates, gold, platinum, silver and other noble metals.

The surface coating of a particular adsorption site may be determined by placing an AFM tip against the material to measure the resiliency of the surface, and correlating the result to the surface coatings applied to the test surface. (See, A. deLoxane, Science Vol. 291, pp. 2561–2562, 2001.) For example, a silicon nitride coating will have a higher surface resiliency than silicon, while a gold coating will have a lower surface resiliency. The surface coating of a particular nanostructure can also be determined by operating the AFM as a conducting AFM, that records both the current through the tip and the force on the tip, measuring the conductivity of the surface material, and comparing the conductivity measurement to known conductivity values for the coating materials applied to the test surface. Similarly, by using a magnetic STM tip, the magnetic properties of the adsorption site can also be measured and compared to known magnetic properties of the coating materials applied to the test surface.

In some embodiments, surfaces that have the same pattern of nanofeatures, the pattern being repeated over an entire chip surface, are desirable for protein discovery. Use of masks in conjunction with one or more of the technologies for fabrication of coating the surface with features, as described supra, can achieve this result as is appropriate to the application.

In order to identify the surface topology of the binding sites of a particular protein, the solution containing the protein molecules is purified to remove other proteins that can adsorb to other sites. Further, analyzing statistically the topographic measurements of a statistically significant number of adsorption sites substantially reduces false results from traces of contaminating proteins.

To speed up the detection of proteins adsorbed to the test surface, the proteins may be marked with a microparticle or dye molecule to make the protein opaque or fluorescent. The use of microparticles and dye molecules as markers for specific proteins is well known in the art. For example, U.S. Pat. No. 5,846,708, issued Dec. 8, 1998, summarizes known methods for binding radionuclide microparticles or covalently binding dye molecules to proteins and DNA, and shows methods of detecting biological molecules in a monolithic array of test sites each containing a molecule probe (e.g. an antibody) that will chemically bind with the biological molecule. The method can include attaching a microparticle or dye molecule to an antibody that will bind to the target protein.

Once the antibody/particle complexes have been allowed to react with the target proteins, the proteins can be identified by detecting the opacity of the microparticle or the fluorescence of the dye molecule when irradiated with light. Applied to this invention, following washing of unadsorbed proteins from the test surface, antibodies or other suitable molecular probe capable of binding to the target protein, which are attached to microparticles or dye molecules, are applied to the test surface. After a time sufficient for the antibodies to bind to target proteins on the test surface, the unadsorbed antibody/microparticle complexes are washed from the surface. Then the proteins are located by illuminating the test surface with light and detecting spots of opacity or fluorescence. Following locating such spots, an AFM is used to identify the specific adsorption sites, and then to determine the precise topology of the adsorption site as described herein. An Atomic Resolution AFM/Optical Microscope which is suitable both for detecting fluorescing dye molecules coupled to adsorbed proteins, and for measuring the topology of adsorption sites is commercially available from Molecular Imaging Corp. (Phoenix, Ariz.), and from Princeton Instruments and Photometrics (Roper Scientific, Trenton, N.J.).

The use of antibodies coupled to opaque particles or dye molecules provides an efficient method for reusing a test surface as a protein detection chip. In this embodiment, following locating adsorption sites for a target protein by the methods described herein, the coordinates of the adsorption sites are used in conjunction with antibody/microparticle complexes and a reader, to detect the presence of target proteins in a sample of unknown constituents. The reader detects the precise coordinates of a protein/antibody/microparticle on the test surface, to rapidly locate and record the adsorption sites for the target protein. Suitable readers include optical scanners, imaging scanners (e.g. charged coupled device (CCD) cameras), laser scanners similar to the laser-reader used in laser-readers used in compact disk player applications, magnetic probe scanners similar to the reader head used in computer magnetic storage devices, and STMs which detect current conducted by a metallic microparticle. The reader is connected to a computer that controls the scanning process, collects and stores the adsorption site coordinate data produced by the reader, and processes the data to identify and recognize patterns of adsorption sites located on the test surface. The reader then is used to survey the test surface at the precise coordinate locations of adsorption sites to detect whether target protein/antibody/microparticle complexes are present.

In a further application, the adsorption sites for a large number of different proteins are identified on a single test surface by repeating the method of this invention for a plurality of different target proteins. Once adsorption sites for several different proteins have been mapped on the test surface, the surface can be used as a protein assay tool by attaching microparticles or dye molecules to proteins present on the surface after the first washing step. In this embodiment, the reader detects the presence of a particular protein by recognizing the pattern that the adsorbed proteins make on the test surface. Since adsorption sites are protein specific, each type of protein will display a unique pattern of adsorption sites, which will enable a reader to simultaneously detect the presence or absence of a large number of proteins in one step.

Another method that facilitates discovery of adsorption sites on a test surface involves attaching to the adsorbed proteins magnetic dipole microparticles, such as any of the types of magnetic particles used in the fabrication of magnetic recording media (e.g. floppy disks) for the computer industry. Magnetic dipole particles can be chemically coupled (by covalent bonds) to antibodies that bind to the target protein. The antibody/magnetic-microparticle complexes are mixed with proteins adsorbed to the test surface, and unbound complexes are removed by washing. A magnetic field reader, similar to the disk drive reader heads used in computer disk drive applications, is used to detect the presence or absence of the resulting protein/antibodylmagnetic-microparticle complexes on the test surface.

Another method that facilitates discovery of binding sites on a test surface is using an AFM with an array of a plurality of sensor microcantilevers, each sensor microcantilever having a surface contacting tip, to simultaneously survey the surface at many points. A thousand-sensor tip AFM for reading nanometer-scale surface features on a terabit capacity data storage device has been described by P. Vettiger, et. al. in "The 'Millipede'—More than one thousand tips for future AFM data storage," IBM Journal of Research & Development, Vol. 44, No. 3 Nov. 22, 1999, which is hereby incorporated by reference in its entirety. The IBM multi-tip AFM reader for terabit capacity data storage applications uses a sensor comprised of an array (e.g. 32 by 32) of microcantilevers operated as thermomechanical AFMs. Thermomechanical AFMs are heated microcantilevers that sense the presence of nanometer-scale structures by the change in thermal conductance between the AFM tip and the surface which results as the distance between the AFM tip and the test surface changes.

AFM microcantilevers may also detect the presence of nanometer-scale structures and proteins by the change in natural frequency induced in the microcantilever by electromagnetic or atomic interactions with the surface, obviating the need for the AFM tip to actually contact the proteins in order to detect them. Because protein molecules have a different (e.g., lower) thermal conductance than the test surface coating, thermomechanical AFMs can detect the presence of proteins adsorbed to the test surface. Since thermomechanical AFMs scan above the surface, a fast scan rate of test surface is provided. An AFM with a multi-tip microcantilever array sensor has the significant advantage of enabling a relatively large (approximately 3 millimeters by 3 millimeters) test surface to be inspected substantially instantaneously, greatly increasing both the size of the test surface, and the number of potential adsorption sites.

An AFM with a multi-tip microcantilever array sensor may also include a positioning table, as herein described, and a fluidics cell, as herein described, so that the assemblage of AFM, computer controller, computer database, positioning table and fluidics cell forms a protein assay apparatus.

The use of antibodies having attached magnetic particles provides a method for rapidly and precisely locating adsorption sites on a test surface, and a method that allows the test surface to be used as a protein assay device. By repeating the methods disclosed herein for discovering adsorption site locations for a plurality of proteins on a single test surface, the test surface can subsequently be used as an assay detector for the plurality of proteins. In this application, a magnetic reader is used to determine the precise location and patterns on the surface of the adsorption sites of specific proteins, after which the reader is used to recognize the patterns on the surface of proteins adsorbed thereto, similar to the method described above for using visual readers. Similarly, opaque microparticles or dye molecules coupled to the proteins would enable the test surface to be used as a protein assay device when combined with a rapid scanning optical reader, such as a laser reader similar to those used in compact disk and digital video disk player applications.

A surface of random nanostructures provides numerous unique configurations that are landmarks for establishing a coordinate grid system. Such landmarks on the test surface and on a coordinate grid system (e.g. a rectilinear coordinate grid measured in nanometers) will enable a computer controller or human operator to return the AFM tip, or other suitable reader, to the same adsorption site time after time. To facilitate the process of identifying proteins adsorbed to the test surface, the test surface can be thoroughly mapped using an AFM, STM or other suitable reader before a sample containing proteins is introduced to the test surface. In this approach, the test surface topology information generated by the AFM, STM or other reader would first be recorded in a computer database. Then during subsequent scanning of the test surface to identify adsorbed proteins, a computer is used to compare the output of the AFM, STM or other reader to the test surface topology database, to automatically identify changes in the test surface topology, the changes indicating the presence of proteins adsorbed to the surface. Since this comparison needs to identify changes to the test surface topology that are of a size only approximately equal to that of the target protein, such a scan can be conducted with lower resolution and therefore at a much faster rate.

Since the inspection area of a test surface is initially positioned under the AFM microcantilever tip using a visual microscope that can resolve features of approximately two microns, it is advantageous in certain embodiments to mark the test surface with a grid of small lines or dots made of an inert material such as gold. Gold dots or lines can be imprinted on the test surface by atomic sputtering gold through a mask, prior to or after the coating of nanometer-scale features is created on the substrate. Dots or lines spaced approximately two to ten microns apart would facilitate locating an AFM inspection area within a particular grid location.

In an embodiment of the methods provided herein, the test surface is fabricated of a transparent or translucent coating of nanoparticles on top of a transparent substrate such as mica or glass. Such a test surface is well suited for inspection using an Atomic Resolution AFM/Optical Microscope that combines an AFM above the test surface with an precision optical microscope which examines the test surface from the bottom. In this embodiment, fluorescent dye molecules are coupled to adsorbed proteins, as described herein, so adsorbed proteins can be roughly located (i.e. within the resolution of the optical microscope which is about two microns) for closer inspection by the AFM. This embodiment would permit rapid detection and inspection of adsorption sites due to several features: the optical microscope has a much larger field of regard than the AFM, permitting adsorption sites to be rapidly located over a larger surface area; fluorescent dye molecules coupled to the adsorbed proteins permit the optical microscope to distinguish adsorbed proteins of the desired type; and the optical and AFM inspections can be performed nearly simultaneously without the need to move the test surface from one instrument to the other. Thus problems locating specific points on the test surface and correlating the views of the two instruments can be avoided.

In another embodiment of the methods provided herein, the test surface is positioned in a fluidics cell within an AFM, with fluidic inlets and outlets that permit solutions and washing agents to be reacted with the test surface without having to move the surface or repositioning the AFM tip. A fluidics cell may be a simple walled structure, such as a rubber or metal-plus-rubber ring, that is positioned on top of the test, surface so the area to be examined is contained within the walls so as to hold a small amount of liquid on top of the test area. The fluidics cell is sufficiently large in diameter so the AFM sensor can fit into it and scan the test surface. The walled structure may include a soft rubber or polymer seating surface which can form a water-tight seal with the test surface. One or more fluid inlets, such as micropipettes, and one or more fluid outlets, such as micropipettes or notches in the walled surfaces, are positioned within the walled structure so solutions can be introduced to and drained from the test surface.

The walled structure and fluidic inlets and outlets may be fabricated as a single unit that can be placed on top of the test surface. Further, the test surface and walled structure may be assembled as a single unit. The walled structure and fluid inlets and outlets may be assembled on a positioning table, as herein described, as a single unit. Integrated fluidics cells and positioning tables may also include thermocouples and electrical heaters to control the temperature of the test surface and solution. Furthermore, the AFM, fluidics cell and positioning table assemblage may be contained within an environmental control enclosure to prevent contamination of the test surface, with fluidic access via inputs and output through the environmental enclosure.

When the methods herein disclosed are accomplished with an AFM incorporating a fluidics cell, the AFM is used to analyze the complete topology of the area of the test surface (i.e. the area within the field of regard of the AFM sensor including the area presented to the AFM sensor by a positioning table) prior to application of a sample, and the topology information so acquired is stored in a computer database. After the test surface topology has been measured, the sample with the protein solution is introduced to the fluidics cell through the inlet port. The protein is permitted to react with the test surface for a period of time, then it is removed from the test surface by draining the protein solution from the outlet while introducing a washing fluid, such a buffer of specified pH and ionic strenght, through the inlet. Following washing, the AFM again scans the test surface within its field of regard to identify adsorbed proteins by comparing the surface topology measurements to the topology measurements in the database. The location and periphery of the adsorption sites is recorded in a computer database using landmark information in the test surface topology database and a coordinate grid system. The topology of the adsorption site is then identified by accessing the topology information from the topology measurements database for the area within the outline of the protein. To confirm the topology of the adsorption site, the adsorbed proteins can be removed from the test surface by a washing step of sufficient stringency, e.g., a buffer capable of removing all bound protein, due to ionic strength, temperature, or other features known to one of ordinary skill in protein separations, by introducing the buffer through the fluidics cell inlet and flushing the fluids out the outlet, followed by a detailed inspection of the adsorption site with the AFM.

Once a test surface has been fabricated, the adsorption sites discovered using the methods described herein and the database of surface structures and adsorption sites has been created, the surface may be replicated in mass production to produce identical surfaces suitable for use as detection and assay tools. This is accomplished by molding the surface using a soft polymer. The mold then can be used to produce multiple copies of the surface using casting or ion deposition methods in a process similar to that used to mass produce compact disks and digital video disks. In other embodiments, an STM can also be used to fabricate replica test surfaces by implementing nanofabrication instructions provided by a computer controller. Thus, a test surface on which the adsorption sites of a large number of different target proteins have been located and the position information stored in a computer database can be used to produce assay sensors for any combination of target proteins in a solution of unknown constituents. In such assay sensors, the test surfaces are used in conjunction with each of a reader capable of detecting the presence of single protein molecules, and a computer capable of comparing the location of adsorbed proteins to the known locations of adsorption sites.

Another embodiment of the inventions herein permits rapid detection of one or more proteins in a sample from a subject that newly appear (or disappear), and that can be correlated with the presence of a particular disease of a plant or animal. Detection can be made without knowledge in advance of the identity or function of the one or more proteins. This method enables producing a device for disease discovery and diagnosis without the need for further advance information, for example, a structure of a protein, the life cycle of the pathogen, or a characteristic of the disease state. In this method, a single test surface, or a plurality of exact replicas of a single test surface, is used to locate all the protein adsorption sites of proteins in a biological sample of a bodily fluid (e.g. a sample of urine, blood, tears, saliva, sap or biopsy tissue sample in which cells have been lysed) from an individual, with the method repeated using the same surface for a statistically significant large number of individuals having a particular disease, and a statistically significant large number of individuals who are free of that disease.

A biological sample of bodily fluids may contain tens of thousands of different types of proteins or protein variants, including certain proteins that are expressed, or fail to be expressed, when an individual subject is suffering from a particular disease state. Using the methods described herein for discovering adsorption sites, the locations of all protein adsorption sites as well as the patterns of protein adsorption on the test surface are determined for each individual, with the location (e.g. the coordinates on an X-Y coordinate grid of the test surface) of each adsorption site recorded in a computer database. While the method involves identifying and recording the adsorption sites, there is no need to further determine the identity of a protein adsorbed to a particular site in order that this method be operative, nor is there a requirement that the adsorption site topology be measured in detail. It is sufficient that adsorption of a protein to a particular site, or failure of adsorption of a protein to a site, can be correlated with the presence of a disease state.

When the adsorption site location coordinates have been recorded for all samples, including samples from the pluralities of each of diseased and nondiseased individual subjects, the adsorption patterns observed on the test surface using samples from those individuals having the specific disease is determined by the unique pattern associated only with the disease, by comparing the adsorption patterns expressed on the test surface in samples from those individuals free of the disease. This may be accomplished by digitizing the patterns of protein adsorption expressed on the test surface exhibited by each sample, using computers to analyze the data to identify disease-specific patterns, and then using statistical analysis to identify the most probable pattern.

The analysis of the adsorption site data may also be accomplished by analyzing statistically all the data for each coordinate grid point on the test surface, with each grid point being a site that is either free of adsorbed protein, or bound to and covered by an adsorbed protein at that site. In this approach, the data from all disease-samples for each grid point is analyzed to determine the probability of the grid point being covered by an adsorbed protein, and the data from all non-disease-samples for each grid point is analyzed to determine the probability of the grid point being covered by an adsorbed protein, and the two probabilities are compared. If there is a significant change between disease and non-disease samples in the probability of the particular grid point being covered by a protein, then that grid point is noted as a disease-specific adsorption site. The disease-specific adsorption site may correspond to a protein that is expressed only by individuals having the disease, or it may correspond to a protein that is normally expressed in healthy individuals but not by individuals having the disease.

Once a test surface has been quantified by the method above such that the disease-specific protein adsorption site locations or adsorption site patterns are known, the test surface, or an exact replica of the test surface, can be used as a diagnostic device. This method involves exposing the test surface (or an exact replica of the test surface) to a sample of a bodily fluid from an individual, then surveying the test surface with a reader capable of recognizing the locations or pattern of adsorption sites associated with the specific disease. With this method, the locations or patterns of adsorption sites required to diagnose the disease can be obtained.

Disease-specific adsorption site locations or patterns identified using an embodiment of this method may involve different adsorption sites for a plurality of types of proteins, all of which can be differentially observed between individuals having the disease and non-diseased individuals. A diagnostic conclusion that is reached on the basis of observations of a plurality of types of proteins can reduce the occurrence of false-positive (Type II error) results. Such false-positive diagnoses can occur with greater frequency using diagnostic methods that detect the presence or absence of only a single protein, which can be indicative but not dispositive of a disease state. Certain diagnostic methods in use, such as the Prostate Specific Antigen (PSA) and tests for HIV, have a high false-positive rate. False-positive results can cause physicians and patients to mistrust diagnostic tests, and can lead to unnecessary patient distress. Therefore, there would be great value in new diagnostic methods that substantially reduce or eliminate the level false-positive diagnoses of current methods.

Once the protein adsorption pattern on a test surface for a particular disease is identified, the specific proteins that form the basis of this diagnostic pattern can be identified, and these proteins can be further enriched or purified using specially fabricated surfaces. Specifically, surfaces with nanostructures matching individual protein binding sites can be manufactured using STM techniques described (see, U.S. Pat. No. 6,123,819, issued Sep. 26, 2000). By fabricating a surface containing many thousands of copies of a given adsorption site, the site being of interest because it is a disease specific adsorption site, a given disease-associated protein can be enriched from a sample. This is achieved by first reacting the sample with the surface, washing off unadsorbed proteins, and then eluting the adsorbed protein into a separate container.

In certain embodiments, the protein can be directly characterized from the disease-specific site on the chip by using a process such as MALDI-TOF. MALDI-TOF is a well-known process for determining chemical constituents of biological molecules, this process being well suited to characterizing proteins adsorbed as herein to a known locus on test surface. With this process, samples are deposited on a smooth metal surface and desorbed into the gas phase as the result of a pulsed laser beam impinging on the surface of the sample (see U.S. Pat. No. 6,057,543, issued May 2, 2000). Hence, specific disease-related proteins can be rapidly purified and characterized.

The surface topology of the proteins can be determined using an AFM according to the methods described herein. By rapidly identifying and concentrating disease-specific proteins associated with a particular disease and providing information on the surface topology, this method can facilitate the rapid development of diagnostic and prognostic techniques to monitor treatment methods, for new or for rapidly mutating pathogens such as HIV, viral influenza, and malaria, as well as develop accurate indicators for maladies such as certain cancer indications that heretofore have evaded efforts to develop reliable early detection diagnostics. This method also permits rapid discovery and purification of novel proteins associated with a given disease, which is important because disease-specific proteins are useful for development of new treatments, new targets for therapeutic agents such as drugs, and new diagnostics and prognostics for the disease. Further, a newly identified disease-related protein can be used as an antigen to obtain antibodies to that protein, by methods that are well-known to one of ordinary skill in the art of immunobiology. Such antibodies may then be used for development of therapeutic treatments, such as for drug delivery as immunoconjugtes, and for diagnostic purposes.

Methods provided herein can be used for identifying binding sites on the surface of pathogens and cells, even in the absence of information on the surface proteins of such pathogens and cells. In this method, a sample containing the target pathogens or other cells is allowed to react with the test surface sufficient for surface proteins to adsorb to complementary sites, after which the unadsorbed components of the sample are removed by washing. An optical microscope or AFM is used to locate the positions of adsorbed pathogens or cells on the test surface. The AFM is further used to measure the topology of the test surface in the area where a pathogen or cell was adsorbed. Given the large size of a pathogen or cell with respect to the protein binding area, this method may not immediately identify the specific protein binding site. Nevertheless, the method will yield useful topology information, for the development of diagnostic devices that can identify the particular pathogen, and for further analysis of surface proteins.

Surface proteins of cells or pathogens are analyzed according to other embodiments by preparing a lysate of units of the pathogen and thereby releasing surface proteins into solution, so that the surface proteins can adsorb with affinity and specificity to sites on the test surface. Units of a pathogen refer to cells, for example, bacterial, protozoan, or fungal cells or spores, or to virions of a virus. Once the topology of a surface protein of a pathogen is determined using the methods herein disclosed, replication of the adsorption site topology on a protein chip as disclosed in U.S. Pat. No. 6,123,819, issued Sep. 26, 2000, will enable detection of individual target pathogen proteins. In addition, the surface protein topology information may be useful for certain medical treatment or drug development purposes, as described herein.

A further embodiment of this invention is the coupling with an AFM of a positioning table for controlling the position of the test surface under the inspection area of an AFM with great precision. A suitable positioning table would have the capability of moving the test surface in two dimensions in steps of about 30 micrometers or less. Numerous precision positioning tables are commercially available for microscope applications as well as for automated assembly of circuit boards. Alternatively, the test surface may be fabricated as a small (e.g. about 1 to about 3 centimeters in diameter) circular disk which can be mounted on a precision turntable positioned on the AFM so the test surface turns underneath the inspection area of the AFM microcantilever tip or tips. Precision turntables have been developed for miniature computer disk drive applications (see for example "IBM's Tiny Microdrive Promises to Put Big Storage Space into Devices like Digital Cameras and PDAs," Popular Science, December 1998, p. 38). Positioning a circular test surface onto a small turntable coupled to an AFM will permit a large test surface to be rapidly scanned for adsorbed proteins. When combined with a multi-tip AFM, a rotating circular test surface would enable the rapid inspection of about $10^{12}$ to about $10^{15}$ potential adsorption sites. It is contemplated that a protein scanning AFM incorporating a moving table for the test surface and multiple AFM tips would be controlled by a computer, possibly a multi-processor computer, with data stored directly to a computer database.

It is further contemplated as part of this invention that the positioning table, whether it is an X-Y positioner or a turntable, may incorporate a fluidics cell as herein described. A fluidics cell would permit conducting the methods described herein while the test surface remains in place on the positioning table, without requiring the test surface to be removed from the AFM/positioning table assembly between steps. It is further contemplated as part of this invention that this embodiment may be implemented in commerce as a whole proteome assay device, incorporating an extensive computer database of proteornic information, a computer-controlled AFM with a single or multi-tip sensor, an integrated fluidics cell and turntable, and a variety of test surfaces, including both random structure surfaces and nanomachined surfaces tailored for specific proteome assays (e.g. human, plant, cattle, etc.).

This invention will enable identifying all proteins expressed in a particular biological sample, a capability which will have significant applications in medical and biological research. Much can be learned about the expression of particular genes by matching expressed proteins to their genomic templates. This invention will permit researchers to rapidly identify known proteins, to discover unknown proteins, and to determine the surface topology of these proteins. By comparing the proteins and protein shapes identified using this invention to known protein X-ray diffraction information, the expressed proteins can be identified and matched to known amino acid sequences and to genomic information available in public and private databases. Using this approach, researchers will be able to identify the genes that are being expressed in a given sample.

A potentially powerful medical diagnostic procedure is enabled by the whole proteome capabilities of this invention. Specifically, this invention will allow a doctor to determine the effectiveness of a particular drug or treatment on an individual, by monitoring the change in protein expression induced by the drug or treatment. This method comprises obtaining a sample from the patient and performing a whole proteome assay using the devices and methods of this invention before prescribing a drug or treatment. After the drug or treatment has been administered for a period of time, another sample is taken and the proteome assay repeated. The physician or therapy provider is able to formulate a prognosis, i.e., to judge the effectiveness of the drug or treatment, by noting whether there has been a change in expression of disease-specific proteins. Equipped with such information, the physician can adjust or maintain the treatment with a better understanding of the biological consequences for the patient, rather than relying solely upon standard dosage guidelines which are based on assumptions and average responses that may not accurately reflect the individual's genetic profile that can cause variation in absorption, distribution, metabolism, excretion, or toxicity of the drug. This diagnostic and treatment monitoring method may have significant implications for cancer and pre-cancer detection, prognosis, and treatment.

While various embodiments of the present invention have been described above and in the drawings, it should be understood that they have been presented only as examples, and not as limitations. In particular, the invention is applicable to all implementations of nanometer-scale surface features as adsorption sites and devices or techniques for discovering adsorption sites on a test surface. Furthermore, the methods herein disclosed for characterizing proteins and developing diagnostic devices for diseases apply equally well to studies and treatment of plants and animal subjects as well as they do for humans. Thus, the breadth and scope of the present invention should not be limited by any of the above-described exemplary embodiments, but should be defined only in accordance with the following claims and their equivalents.

I claim:

1. A method for discovering protein adsorption sites on a surface, comprising:

providing a test surface having a surface topology comprised of a random distribution of randomly shaped nanostructures of a size from about $10^{-10}$ meters to about $10^{-8}$ meters in width, height, depth and spacing;

exposing the test surface to a solution of a substantially purified protein, the solution remaining in contact with the surface sufficiently long to enable protein molecules to adsorb to adsorption sites;

removing the solution with unadsorbed protein molecules from the test surface; and identifying the protein adsorption sites by detecting the presence of adsorbed protein molecules, to locate protein molecules adsorbed to the test surface.

2. The method according to claim 1, further comprising after identifying the protein adsorption sites, removing the protein molecules adsorbed to the test surface, and measuring the surface topology of at least one the identified adsorption site.

3. The method according to claim 2, further comprising analyzing statistically the surface topology of a statistically significant number of a plurality of identified adsorption sites to determine a most probable adsorption site topology.

4. The method according to claim 3, further comprising storing the most probable adsorption site topology in a computer database.

5. The method according to claim 2, wherein measuring the surface topology further comprises using one or more of the group consisting of: a microcantilever, an atomic force microscope, a scanning tunneling microscope, a magnetic resonance force microscope, a thermomechanical atomic force microscope, and a multi-tip atomic force microscope.

6. A cluster of randomly shaped nanostructures having the surface topology comprising the protein adsorption site identified according to the method of claim 2.

7. The method according to claim 1, wherein detecting the presence of adsorbed protein molecules is using a microcantilever.

8. The method according to claim 1, wherein detecting the presence of adsorbed protein molecules is using an atomic force microscope.

9. The method according to claim 1, wherein detecting the presence of adsorbed protein molecules is using a scanning tunneling microscope.

10. The method according to claim 1, wherein detecting the presence of adsorbed protein molecules is using a magnetic resonance force microscope.

11. The method according to claim 1, wherein detecting the presence of adsorbed protein molecules is using a thermomechanical atomic force microscope.

12. The method according to claim 1, wherein detecting the presence of adsorbed protein molecules is using a multi-tip atomic force microscope.

13. The method according to claim 1, further comprising coupling a microparticle to protein molecules adsorbed to the test surface.

14. The method according to claim 1, wherein a plurality of different surface coatings is deposited on the test surface, each coating having a characteristic resiliency, and further comprising determining which of said surface coatings is deposited on the identified adsorption sites by measuring the resiliency of the deposited surface coatings using an atomic force microscope.

15. The method according to claim 1, wherein prior to exposing the test surface to a protein, a plurality of different surface coatings is deposited on the test surface, each coating having a characteristic conductivity, and further comprising determining which of the surface coatings is deposited on the identified adsorption sites by measuring the conductivity of the deposited surface coatings using a conducting atomic force microscope.

16. The method according to claim 1, wherein in providing a test surface, the nanostructures are not randomly distributed, and the nanostructures have a width, a height, a depth, and a spacing in an identical pattern distributed regularly on the test surface.

17. The method according to claim 1, wherein detecting the presence of adsorbed protein molecules is using microparticles coupled to protein molecules adsorbed to the test surface.

18. A method for determining a topology of protein binding sites, comprising:

providing a test surface having a surface topology having a random distribution of randomly shaped nanostructures of a size from about $10^{-10}$ meters to about $10^{-8}$ meters in width, height, depth and spacing;

depositing a solution containing substantially a single type of protein molecules on the test surface, and permitting the solution to remain sufficiently long to enable the protein molecules to adsorb to protein binding sites on the test surface;

removing unadsorbed proteins from the test surface;

using an atomic force microscope for identifying a location of the adsorbed protein molecules on the test surface; and determining the topology that is complementary to the surface topology measurements of the identified adsorption sites.

19. The according to claims 18, further comprising, prior to depositing a solution of proteins on the test surface, using an atomic force microscope to obtain a plurality of surface topology measurements of the test surface, and recording the surface topology measurements in a computer database.

20. The method according to any of claims 18 and 19, further comprising analyzing a statistically significant number of the surface topology measurements of the identified adsorption sites, to determine a most probable adsorption site topology and a most probable complementary protein surface topology of the single type of protein.

* * * * *